(12) United States Patent
Timken (10) Patent No.: US 12,359,135 B2
(45) Date of Patent: Jul. 15, 2025

(54) CIRCULAR ECONOMY FOR PLASTIC WASTE TO POLYPROPYLENE AND BASE OIL VIA REFINERY HYDROCRACKING UNIT

(71) Applicant: Chevron U.S.A. Inc., San Ramon, CA (US)

(72) Inventor: Hye-Kyung C. Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 18/128,366

(22) Filed: Mar. 30, 2023

(65) Prior Publication Data
US 2023/0313052 A1    Oct. 5, 2023

Related U.S. Application Data

(60) Provisional application No. 63/326,707, filed on Apr. 1, 2022.

(51) Int. Cl.
*C10G 1/00* (2006.01)
*C08F 10/06* (2006.01)
(Continued)

(52) U.S. Cl.
CPC .............. *C10G 47/34* (2013.01); *C08F 10/06* (2013.01); *C10G 1/002* (2013.01); *C10G 45/72* (2013.01);
(Continued)

(58) Field of Classification Search
CPC .............. C10G 2300/1003; C10G 2300/4081
See application file for complete search history.

(56) References Cited

U.S. PATENT DOCUMENTS 3,845,157 A    10/1974  Woo
4,642,401 A     2/1987  Coenen et al.
(Continued)

FOREIGN PATENT DOCUMENTS

DE    43 29 436 C1    3/1995
EP    0 620 264 A2   10/1994
(Continued)

OTHER PUBLICATIONS

Machine Translation of abstract of JPH08337782A (Year: 1996).*
(Continued)

*Primary Examiner* — Ellen M McAvoy
*Assistant Examiner* — Ming Cheung Po
(74) *Attorney, Agent, or Firm* — E. Joseph Gess; Melissa M. Hayworth; Terrence M. Flaherty (57) ABSTRACT

Provided is a continuous process for converting waste plastic into recycle for polypropylene polymerization. The process comprises selecting waste plastics containing polyethylene and/or polypropylene and preparing a stable blend of petroleum and the selected plastic. The amount of plastic in the blend comprises no more than 20 wt. % of the blend. The blend is passed to a refinery hydrocracking unit. A liquid petroleum gas $C_3$ olefin/paraffin mixture is recovered from the hydrocracking unit. The $C_3$ paraffins and $C_3$ olefins are separated into different fractions with the $C_3$ olefin fraction passed to a propylene polymerization reactor, and the $C_3$ paraffin fraction passed optionally to a dehydrogenation unit to produce additional propylene. A heavy fraction can also be recovered from the hydrocracking unit and passed to an isomerization dewaxing unit to prepare base oil.

31 Claims, 6 Drawing Sheets

(51) Int. Cl.
*C10G 45/72* (2006.01)
*C10G 47/34* (2006.01)

(52) U.S. Cl.
CPC ........... *C10G 2300/1003* (2013.01); *C10G 2300/4081* (2013.01); *C10G 2400/02* (2013.01); *C10G 2400/04* (2013.01); *C10G 2400/08* (2013.01)

(56) References Cited

U.S. PATENT DOCUMENTS

| | | | |
|---|---|---|---|
| 5,849,964 | A | 12/1998 | Holighaus et al. |
| 6,143,940 | A | 11/2000 | Miller et al. |
| 6,150,577 | A | 11/2000 | Miller et al. |
| 6,288,296 | B1 | 9/2001 | Miller et al. |
| 6,774,272 | B2 | 8/2004 | Miller |
| 6,822,126 | B2 | 11/2004 | Miller |
| 7,834,226 | B2 | 11/2010 | Miller |
| 8,088,961 | B2 | 1/2012 | Miller |
| 8,404,912 | B1 | 3/2013 | Miller |
| 8,696,994 | B2 | 4/2014 | Miller |
| 2013/0267745 | A1 | 10/2013 | Schrod et al. |
| 2014/0228205 | A1 | 8/2014 | Narayanaswamy et al. |
| 2015/0258713 | A1 | 9/2015 | Valdmaa et al. |
| 2016/0264885 | A1 | 9/2016 | Narayanaswamy et al. |
| 2016/0362609 | A1 | 12/2016 | Ward et al. |
| 2018/0201847 | A1* | 7/2018 | Kohli ............... C10G 47/22 |
| 2019/0023997 | A1 | 1/2019 | Sundaram |
| 2019/0161683 | A1 | 5/2019 | Narayanaswamy et al. |
| 2020/0172716 | A1 | 6/2020 | Pehlert et al. |
| 2021/0087473 | A1 | 3/2021 | Pradeep et al. |
| 2021/0130699 | A1 | 5/2021 | Bitting et al. |
| 2021/0189248 | A1 | 6/2021 | Timken |
| 2021/0189249 | A1 | 6/2021 | Timken |
| 2021/0189250 | A1 | 6/2021 | Timken |
| 2021/0189252 | A1 | 6/2021 | Timken |
| 2021/0189253 | A1* | 6/2021 | Timken ............... C10G 11/18 |
| 2021/0189254 | A1* | 6/2021 | Timken ............... C10M 109/02 |
| 2021/0332299 | A1 | 10/2021 | Timken |
| 2021/0332300 | A1 | 10/2021 | Timken |
| 2022/0041940 | A1* | 2/2022 | Pradeep ............... C10G 11/182 |
| 2022/0098490 | A1 | 3/2022 | Abbott et al. |
| 2022/0267685 | A1 | 8/2022 | Babu et al. |
| 2022/0314497 | A1 | 10/2022 | Ramanujam et al. |

FOREIGN PATENT DOCUMENTS

| | | | |
|---|---|---|---|
| EP | 1 707 614 | A1 | 4/2006 |
| JP | H08337782 | A * | 12/1996 |
| WO | 2013/169367 | A1 | 11/2013 |
| WO | 2016/059565 | A2 | 4/2016 |
| WO | 2022/020151 | A1 | 1/2022 |

OTHER PUBLICATIONS

International Search Report and Written Opinion issued in International Patent Application No. PCT/US2023/016853, Jul. 11, 2023.
International Preliminary Report on Patentability issued in corresponding International Patent Application No. PCT/US2023/016853, Sep. 24, 2024.
International Search Report and Written Opinion issued in related International Patent Application No. PCT/US2023/016850, Jul. 3, 2023.
International Preliminary Report on Patentability issued in related International Patent Application No. PCT/US2023/016850, Sep. 24, 2024.
International Search Report and Written Opinion issued in related International Patent Application No. PCT/US2023/016833, Jun. 30, 2023.
International Preliminary Report on Patentability issued in related International Patent Application No. PCT/US2023/016833, Sep. 24, 2024.
International Search Report and Written Opinion issued in related International Patent Application No. PCT/US2023/016839, Jul. 5, 2023.
International Preliminary Report on Patentability issued in related International Patent Application No. PCT/US2023/016839, Sep. 24, 2024.
International Search Report and Written Opinion issued in related International Patent Application No. PCT/US2023/016857, Jul. 20, 2023.
International Preliminary Report on Patentability issued in related International Patent Application No. PCT/US2023/016857, Sep. 24, 2024.
International Search Report and Written Opinion issued in related International Patent Application No. PCT/US2023/016862, Jul. 11, 2023.
International Preliminary Report on Patentability issued in related International Patent Application No. PCT/US2023/016862, Sep. 24, 2024.
International Search Report and Written Opinion issued in related International Patent Application No. PCT/US2023/016869, Jul. 20, 2023.
International Preliminary Report on Patentability issued in related International Patent Application No. PCT/US2023/016869, Sep. 24, 2024.
International Search Report and Written Opinion issued in related International Patent Application No. PCT/US2023/069864, Nov. 14, 2023.
International Search Report and Written Opinion issued in related International Patent Application No. PCT/US2023/069871, Nov. 14, 2023.
International Search Report and Written Opinion issued in related International Patent Application No. PCT/US2023/069874, Nov. 16, 2023.
International Search Report and Written Opinion issued in related International Patent Application No. PCT/US2023/069862, Jan. 18, 2024.
International Search Report and Written Opinion issued in related International Patent Application No. PCT/US2023/069876, Nov. 16, 2023.
International Search Report and Written Opinion issued in related International Patent Application No. PCT/US2023/069881, Nov. 16, 2023.

* cited by examiner

CIRCULAR ECONOMY FOR PLASTIC WASTE TO POLYPROPYLENE AND BASE OIL VIA REFINERY HYDROCRACKING UNIT

CROSS REFERENCE TO RELATED APPLICATIONS

The present application claims priority to U.S. Provisional Application No. 63/326,707, filed Apr. 1, 2022, the complete disclosure of which is incorporated herein by reference in its entirety.

BACKGROUND

The world has seen extremely rapid growth of plastics production. According to PlasticsEurope Market Research Group, the world plastics production was 335 million tons in 2016, 348 million tons in 2017, 359 million tons in 2018, and 367 million tons in 2020. According to McKinsey & Company, the global plastics-waste volume is estimated to be 460 million tons per year by 2030 if the current trajectory continues.

Single use plastic waste has become an increasingly important environmental issue. At the moment, there appear to be few options for recycling polyethylene and polypropylene waste plastics to value-added chemical and fuel products. Currently, only a small amount of polyethylene and polypropylene is recycled via chemical recycling, where recycled and cleaned polymer pellets are pyrolyzed in a pyrolysis unit to make fuels (naphtha, diesel), stream cracker feed or slack wax. The majority, greater than 80%, is incinerated, land filled or discarded.

The current method of chemical recycling via pyrolysis cannot make a big impact for the plastics industry. The current pyrolysis operation produces poor quality fuel components (naphtha and diesel range products), but the quantity is small enough that these products can be blended into fuel supplies. However, this simple blending cannot continue if very large volumes of waste polyethylene and polypropylene is to be recycled to address environmental issues. The products as produced from a pyrolysis unit are of too poor quality to be blended in large amounts in transportation fuels.

Processes are known which convert waste plastic into hydrocarbon lubricants. For example, U.S. Pat. No. 3,845,157 discloses cracking of waste or virgin polyolefins to form gaseous products such as ethylene/olefin copolymers which are further processed to produce synthetic hydrocarbon lubricants. U.S. Pat. No. 4,642,401 discloses the production of liquid hydrocarbons by heating pulverized polyolefin waste at temperatures of 150-500° C. and pressures of 20-300 bars. U.S. Pat. No. 5,849,964 discloses a process in which waste plastic materials are depolymerized into a volatile phase and a liquid phase. The volatile phase is separated into a gaseous phase and a condensate. The liquid phase, the condensate and the gaseous phase are refined into liquid fuel components using standard refining techniques. U.S. Pat. No. 6,143,940 discloses a procedure for converting waste plastics into heavy wax compositions. U.S. Pat. No. 6,150,577 discloses a process of converting waste plastics into lubricating oils. EP0620264 discloses a process for producing lubricating oils from waste or virgin polyolefins by thermally cracking the waste in a fluidized bed to form a waxy product, optionally using a hydrotreatment, then catalytically isomerizing and fractionating to recover a lubricating oil.

U.S. Pub. No. 2021/0130699 discloses processes and systems for making recycle content hydrocarbons from recycled waste material. The recycle waste material is pyrolyzed to form a pyrolysis oil composition, at least a portion of which may then be cracked to form a recycle olefin composition.

Other documents which relate to processes for converting waste plastic into lubricating oils include U.S. Pat. Nos. 6,288,296; 6,774,272; 6,822,126; 7,834,226; 8,088,961; 8,404,912 and 8,696,994; and U.S. Patent Application Publication Nos. 2019/0161683; 2016/0362609; and 2016/0264885. The foregoing patent documents are incorporated herein by reference in their entirety.

Globally, recycling or upcycling of plastic waste has gained great interest to save resources and the environment. Mechanical recycling of plastic waste is rather limited due to different types, properties, additives, and contaminants in the collected plastics. Usually, the recycled plastics are of degraded quality. Chemical recycling to the starting material or value-added chemicals has emerged as a more desirous route.

However, in order to achieve chemical recycling of single use plastics in an industrially significant quantity to reduce its environmental impact, more robust processes are needed. The improved processes should establish "circular economy" for the waste polyethylene and polypropylene plastics where the spent waste plastics are recycled effectively back as starting materials for the polymers or value-added chemicals or fuels.

SUMMARY

Provided is a continuous process for converting waste plastic into recycle for polypropylene polymerization. The process comprises selecting waste plastics containing polyethylene and/or polypropylene. These waste plastics are blended with a petroleum feed material. The resulting blend is generally a stable blend and a homogenous mixture, particularly at a temperature below the melting point of the waste plastic. The blend comprises about 20 wt. % or less of the selected waste plastic. The blend is then passed together with conventional refinery hydrocarbon feed, such as VGO, to a hydrocracking unit in a refinery.

The incorporation of the process with an oil refinery is an important aspect of the present process and allows the creation of a circular economy with a single use waste plastic such as polypropylene. Thus, the blend is passed to a refinery hydrocracking unit. The blend is passed at a temperature above its pour point in order to be able to pump the blend to the refinery hydrocracking unit. The blend is heated above the melting point of the plastic before injected to the hydrocracking unit. A LPG stream comprising $C_3$ hydrocarbons is recovered from the hydrocracking unit. The $C_3$ stream can be passed onto a propane/propylene splitter to separate $C_3$ paraffins and $C_3$ olefins. The $C_3$ olefin is passed to a propylene polymerization reactor to produce polypropylene, and the $C_3$ paraffins are sent to a dehydrogenation unit to produce additional propylene. A heavy fraction is also recovered from the hydrocracking unit, which fraction is passed to an isomerization/dewaxing unit. Good base oil can be recovered from the dewaxing unit, which can be sent for further processing to a hydrofinishing unit to create a truly premium base oil.

The refinery will generally have its own hydrocarbon feed flowing through the refinery units. An important aspect of the present process is to not negatively impact the operation of the refinery. The refinery must still produce valued chemicals and fuels. Otherwise, the incorporation of the process with an oil refinery would not be a workable solution. The flow volume must therefore be carefully observed.

The flow volume of the waste plastic/petroleum blend to the refinery units can comprise any practical or accommodating volume % of the total flow to the refinery units. Generally, the flow of the blend can be up to about 100 vol. % of the total flow, i.e., the blend flow is the entire flow, with no refinery flow. In one embodiment, the flow of the blend is an amount up to about 50 vol. % of the total flow, i.e., the refinery flow and the blend flow.

Among other factors, it has been found that by adding refinery operations one can efficiently and effectively recycle plastic waste while also complementing the operation of a refinery in the preparation of higher value products such as gasoline, jet fuel, base oil and diesel. But also, by adding refinery operations it has been found that clean propane and propylene can be efficiently and effectively produced from the waste plastics for ultimate polypropylene polymer production. Positive economics are realized for the overall process from recycled plastics to a polypropylene product with product quality identical to that of virgin polymer. The present process also offers the ability of recycling the waste plastics to prepare good/premium base oil, while also preparing the polypropylene products.

DETAILED DESCRIPTION

In the present process, provided is a method to recycle waste polyethylene and/or polypropylene back to virgin polypropylene to establish a circular economy by combining distinct industrial processes. And in one embodiment, premium base oil can be obtained due to integration of the process with a refinery. A substantial portion of polyethylene and polypropylene polymers are used in single use plastics and get discarded after use. The single use plastic waste has become an increasingly important environmental issue. At the moment, there appear to be few options for recycling polyethylene and polypropylene waste plastics to value-added chemicals and fuel products. Currently, only a small amount of polyethylene/polypropylene is recycled via chemical recycling, where recycled and cleaned polymer pellets are pyrolyzed in a pyrolysis unit to make fuels (naphtha, diesel), steam cracker feed or slack wax.

Polypropylene is used widely in various consumer and industrial products. Polypropylene is the second-most widely produced commodity plastic after polyethylene with its mechanical ruggedness and high chemical resistance. Polypropylene is widely used in packaging, film, fibers for carpets and clothing, molded articles and extruded pipes. Today, only a small portion of spent polypropylene products is collected for recycling, due to the inefficiencies and ineffectiveness of the recycling efforts discussed above.

Figure 1:
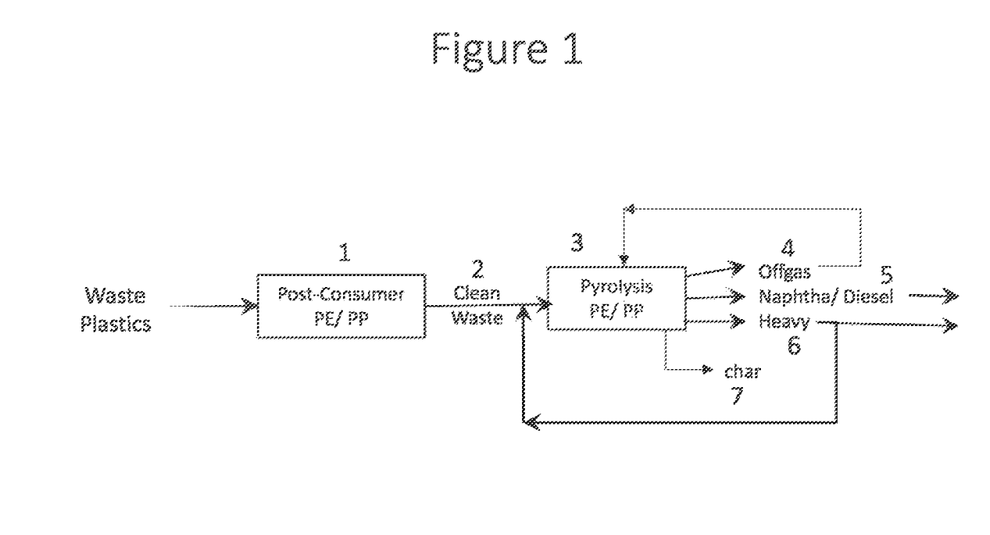
FIG. 1 depicts the current practice of pyrolyzing waste plastics to produce fuel or wax (base case).

FIG. 1 shows a diagram of the pyrolysis of waste plastics fuel or wax that is generally operated in the industry today. Generally, the waste plastics are sorted together 1. The cleaned plastic waste 2 is converted in a pyrolysis unit 3 to offgas 4 and pyrolysis oil (liquid product). The offgas 4 from the pyrolysis unit 3 is used as fuel to operate the pyrolysis unit. An on-site distillation unit separates the pyrolysis oil to produce naphtha and diesel 5 products which are sold to fuel markets. The heavy pyrolysis oil fraction 6 is recycled back to the pyrolysis unit 3 to maximize the fuel yield. Char 7 is removed from the pyrolysis unit 3. The heavy fraction 6 is rich in long chain, linear hydrocarbons, and is very waxy (i.e., forms paraffinic wax upon cooling to ambient temperature). Wax can be separated from the heavy fraction 6 and sold to the wax markets.

The present process, however, does not pyrolyze the waste plastic. Rather, a stable blend of petroleum feedstock and the waste plastic is prepared. Thus, the pyrolysis step can be avoided, which is a significant energy savings.

The present blend can be prepared in a hot blend preparation unit where the operating temperature is above the melting point of the plastic (about 150-250° C.), to make a hot homogeneous liquid blend of plastic and oil. The hot homogeneous liquid blend of plastic and oil can be fed directly to the refinery units.

Alternatively, a blend is prepared in a stable blend preparation unit where the hot homogeneous liquid blend is cooled to ambient temperature in a controlled manner to allow for easy storage and transportation. By using this method, a stable blend can be prepared at a facility away from a refinery and can be transported to a refinery unit. Then the stable blend is heated above the melting point of the plastic to feed to the refinery conversion unit. The stable blend is a physical mixture of microcrystalline plastic particles finely suspended in the petroleum-based oil. The mixture is stable, and the plastic particles do not settle or agglomerate upon storage for extended period.

What is meant by heating the blend to a temperature above the melting point of the plastic is clear when a single plastic is used. However, if the waste plastic comprises more than one waste plastic, then the melting point of the plastic with the highest melting point is exceeded. Thus, the melting points of all plastics must be exceeded. Similarly, if the blend is cooled below the melting point of the plastic, the temperature must be cooled below the melting points of all plastics comprising the blend.

Compared with the pyrolysis unit, these blend preparation units operate at a much lower temperature (~500-600° C. vs. 120-250° C.). Thus, the present process is a far more energy efficient process in preparing a refinery feedstock derived from waste plastic than a thermal cracking process such as pyrolysis.

The use of the present waste plastic/petroleum blend further increases the overall hydrocarbon yield obtained from the waste plastic. This increase in yield is significant. The hydrocarbon yield using the present blend offers a hydrocarbon yield that can be as much as 98%. To the contrary, pyrolysis produces a significant amount of light product from the plastic waste, about 10-30 wt. %, and about 5-10 wt. % of char. These light hydrocarbons are used as fuel to operate the pyrolysis plant, as mentioned above. Thus, the liquid hydrocarbon yield from the pyrolysis plant is at most 70-80%.

When the present blend is passed into the refinery units, such as a crude unit, only a minor amount of offgas is produced. Refinery units, such as hydrocracking units, use catalytic cracking processes that are different from the thermal cracking process used in pyrolysis. With catalytic processes, the production of undesirable light-end byproducts such as methane and ethane is minimized. Refinery units have efficient product fractionation and are able to utilize all hydrocarbon products streams efficiently to produce high value materials. Refinery co-feeding will produce only about 2% of offgas ($H_2$, methane, ethane, ethylene). The $C_3$ and $C_4$ streams are captured to produce useful products such as circular polymer products, while other hydrocarbon streams can be captured to produce quality fuel products, including base oils. Thus, the use of the present petroleum/plastic blend offers increased hydrocarbons from the plastic waste, as well as a more energy efficient recycling process compared to a thermal process such as pyrolysis.

The present process converts single use waste plastic in large quantities by integrating the waste plastic blended with petroleum product streams into an oil refinery operation. The resulting processes produce the feedstocks for the polymers (liquid petroleum gas (LPG), $C_3$ olefin stream for a propylene polymerization unit), high quality gasoline, diesel, jet fuel, and/or quality base oil.

Generally, the present process provides a circular economy for polypropylene plants. Polypropylene is produced via polymerization of pure propylene. Clean propylene can be made from a propane dehydrogenation unit. Also, propylene can be obtained from an oil refinery crude unit, from which a mix of propylene and propane liquefied petroleum gas (LGP) can be recovered. Pure propylene can be separated from the mix using a propane/propylene splitter, a high efficiency distillation column (PP splitter).

By adding refinery operations to upgrade the waste plastic to higher value products (gasoline, jet fuel, diesel, and base oil) and to produce clean propane and propylene for ultimate polypropylene polymer production, positive economics are realized for the overall process of recycled plastics to polypropylene products with product quality identical to that of the virgin polymer. And, by integrating the present recycle process with an oil refinery operation, a more energy efficient and effective process is achieved while avoiding any issues with the refinery operation.

The integration of a refinery operation becomes quite important in another aspect. Waste plastics contain contaminants, such as calcium, magnesium, chlorides, nitrogen, sulfur, dienes, and heavy components, which products cannot be used in a large quantity for blending in transportation fuels. It has been discovered that by having these products go through the refinery units, the contaminants can be captured in pre-treating units and their negative impacts diminished. The fuel components can be further upgraded with appropriate refinery units using chemical conversion processes, with the final transportation fuels produced in the integrated process being of higher quality and meeting the fuels quality requirements. The integrated process will generate a much cleaner and more pure propane stream for the propane dehydrogenation unit and ultimately for polypropylene production. These large on-spec productions allow "cyclical economy" for the recycle plastics to be feasible.

The carbon in and out of the refinery operations are "transparent," meaning that all the molecules from the waste plastic do not necessarily end up in the exact olefin product cycled back to the polyolefin plants, but are nevertheless assumed as "credit" as the net "green" carbon in and out of the refinery is positive. With these integrated processes, the amount of virgin feeds needed for polypropylene plants are reduced significantly.

In some cases, the conversion of waste plastic into clean fuels and base oil takes less energy than production of fuels and base oil from a virgin petroleum feedstock. As the collection and processing of waste plastic improves the gain in energy efficiencies will further improve. The fuels and base oil produced from a blend of waste plastic and oil will have recycle content and lower carbon footprints than corresponding fuels and base oil made from pure petroleum feedstock. The present process can produce clean gasoline, jet fuel, diesel, marine oil and base oil with recycle content and a lower $CO_2$ (lower carbon) footprint from waste plastic.

Figure 2:
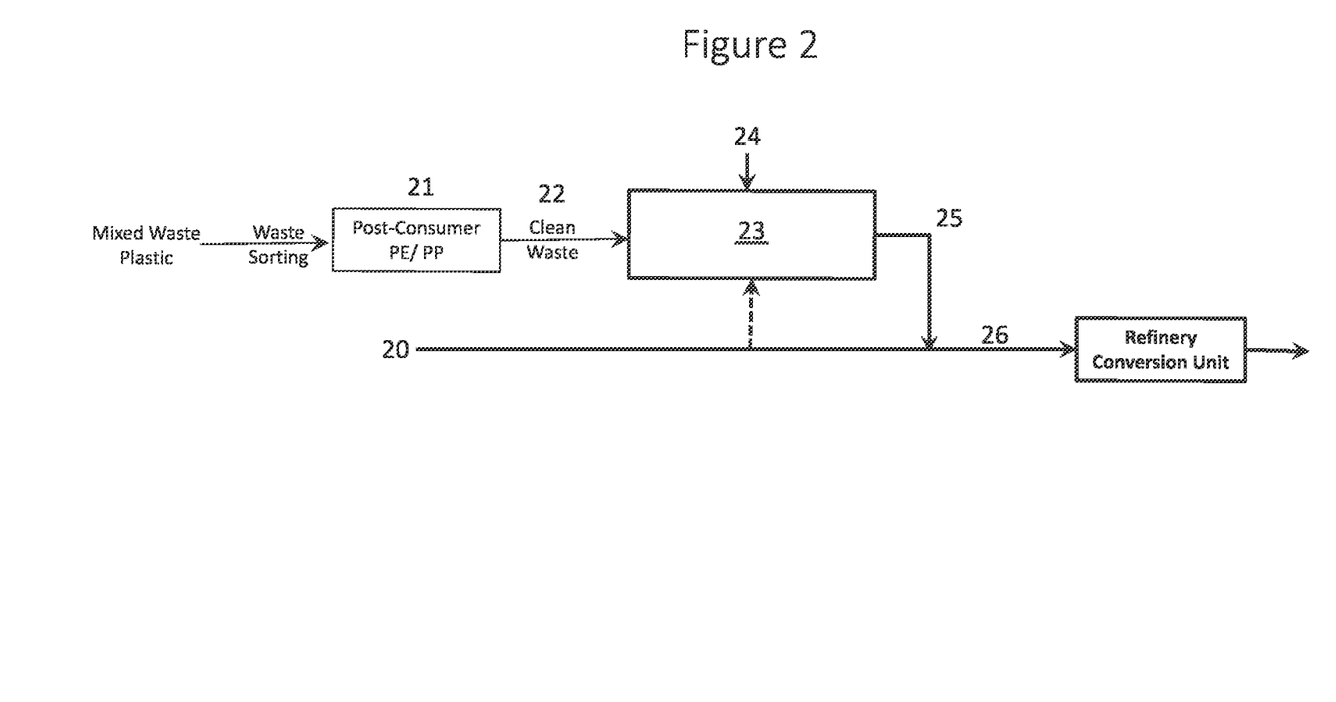
FIG. 2 depicts a present process of preparing a hot homogeneous liquid blend of plastic and petroleum feedstock and how the blend can be fed to a refinery conversion unit.

FIG. 2 illustrates a method for preparing a hot homogenous blend of plastic and petroleum feedstock for use in the present process for direct injection to a refinery hydrocracking unit where a hot, homogeneous liquid blend of plastic and oil is prepared in a hot blend preparation unit. The preferred range of the plastic composition in the blend is about 1-20 wt. %. If high molecular weight polypropylene (average molecular weight of 250,000 or greater) waste plastic or high-density polyethylene (density above 0.93 g/cc) is used as the predominant waste plastic, e.g., at least 50 wt. %, then the amount of waste plastic used in the blend is more preferably about 10 wt. %. The reason being that the pour point and viscosity of the blend would be high.

The preferred conditions for the hot homogeneous liquid blend preparation include heating the plastic above the melting point of the plastic while vigorously mixing with a petroleum feedstock. The preferred process conditions include heating to a 250-500° F. temperature, with a residence time of 5-240 minutes at the final heating temperature, and 0-10 psig atmospheric pressure. This can be done in the open atmosphere as well as preferably under an oxygen-free inert atmosphere.

Referring to FIG. 2 of the Drawings, a stepwise preparation process of preparing the hot homogeneous liquid blend is shown. Mixed waste plastic is sorted to create postconsumer waste plastic 21 comprising polyethylene and/or polypropylene. The waste plastic is cleaned 22 and then mixed with an oil 24 in a hot blend preparation unit 23. After the mixing in 23, the homogeneous blend of the plastic and oil is recovered 25. Optionally a filtration device may be added (not shown) to remove any undissolved plastic particles or any solid impurities present in the hot liquid blend. The hot blend of the plastic and oil can be then combined with a refinery feedstock, such as vacuum gas oil (VGO) 20, and become a mixture of the plastic/oil blend and VGO, 26, which can then be passed to a refinery hydrocracking unit.

Figure 3:
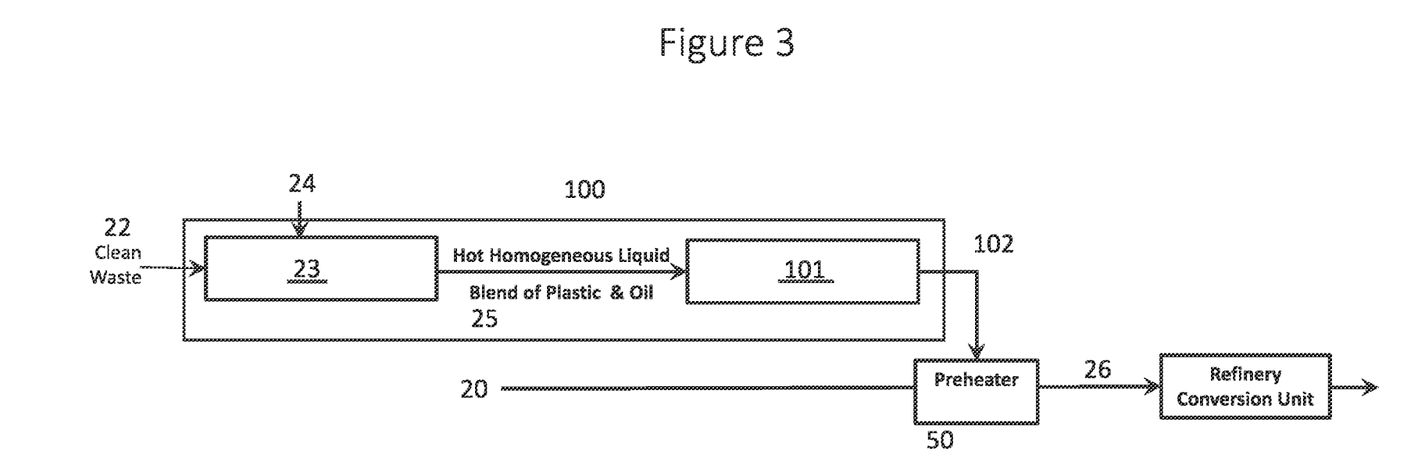
FIG. 3 depicts in detail the stable blend preparation process and how the stable blend can be fed to a refinery conversion unit.

FIG. 3 illustrates a method for preparing a stable blend of plastic and oil for use in the present process. The stable blend is made in a stable blend preparation unit by a two-step process. The first step produces a hot, homogeneous liquid blend of plastic melt and petroleum feedstock, the step identical to the hot blend preparation described in FIG. 2. The preferred range of the plastic composition in the blend is about 1-20 wt. %. If high molecular weight polypropylene (average molecular weight of 250,000 or greater) waste plastic or high-density polyethylene (density above 0.93 g/cc) is used as the predominant waste plastic, e.g., at least 50 wt. %, then the amount of waste plastic used in the blend is more preferably about 10 wt. %. The reason being that the pour point and viscosity of the blend would be high.

The preferred conditions for the hot homogeneous liquid blend preparation include heating the plastic above the melting point of the plastic while vigorously mixing with a petroleum feedstock. The preferred process conditions include heating to a 250-500° F. temperature, with a residence time of 5-240 minutes at the final heating temperature, and 0-10 psig atmospheric pressure. This can be done in the open atmosphere as well as preferably under an oxygen-free inert atmosphere.

In the second step, the hot blend is cooled down below the melting point of the plastic while continuously vigorously mixing with petroleum feedstock, and then further cooling to a lower temperature, preferably ambient temperature, to produce a stable blend of plastic and oil.

It has been found that the stable blend is an intimate physical mixture of plastic and petroleum feedstock. The plastic is in a "de-agglomerated" state. The plastic maintains a finely dispersed state of solid particles in petroleum feedstock at temperatures below the melting point of the plastic, and particularly at ambient temperatures. The blend is stable and allows easy storage and transportation. At a refinery, the stable blend is heated in a preheater above the melting point of the plastic to produce a hot, homogenous liquid blend of the plastic and petroleum. The hot liquid blend can then be fed to a refinery hydrocracking unit as a cofeed with conventional refinery feed.

In FIG. 3, further details of the stable blend preparation are shown. The stable blend is made in a stable blend preparation unit 100 by a two-step process. As shown, clean waste 22 is passed to the stable blend preparation unit 100. The selected plastic waste 22 is heated and mixed with a refinery feedstock oil 24. The plastic waste is heated above the melting point of the plastic to melt the plastic. The petroleum feedstock is mixed with the heated plastic at 23. The mixing is often quite vigorous. The mixing and heating conditions can generally comprise heating at a temperature in the range of about 250-500° F., with a residence time of 5-240 minutes at the final heating temperature. The heating and mixing can be done in the open atmosphere or under an oxygen-free inert atmosphere. The result is a hot, homogenous liquid blend of plastic and oil 25. Optionally a filtration device may be added (not shown) to remove any undissolved plastic particles or any solid impurities present in the hot homogeneous liquid blend.

The hot blend 25 is then cooled below the melting point of the plastic while continuing the mixing of the plastic with the petroleum oil feedstock 101. Cooling generally continues, usually to an ambient temperature, to produce a stable blend of the plastic and oil 102. At a refinery, the stable blend can be fed to a preheater, 50, which heats the blend above the melting point of the plastic to produce a mixture of plastic/oil blend and VGO, 26, which is then fed to a refinery conversion unit, such as a hydrocracking unit.

Figure 4:
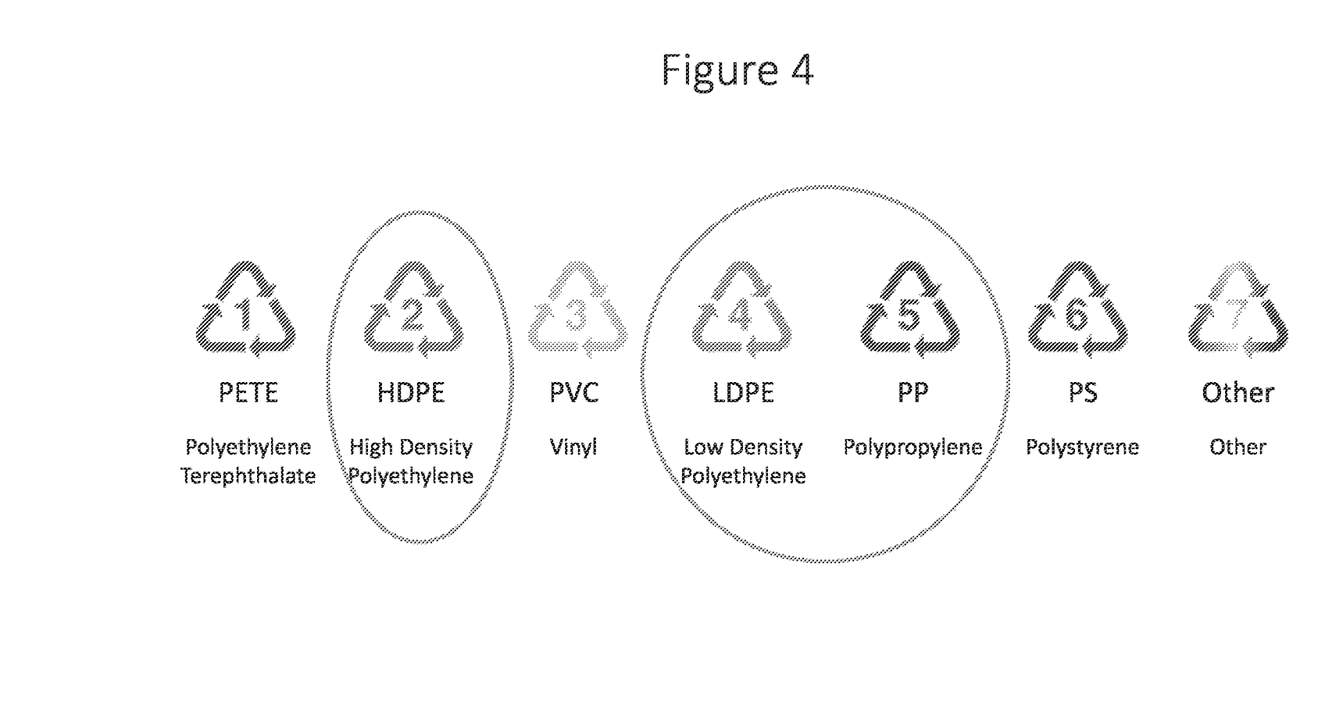
FIG. 4 depicts the plastic type classification for waste plastics recycling.

The preferred plastic starting material for the present process is sorted waste plastics containing predominantly polyethylene and polypropylene (plastics recycle classification types 2, 4, and 5). The pre-sorted waste plastics are washed and shredded or pelleted to feed to a blend preparation unit. FIG. 4 depicts the plastic type classification for waste plastics recycling. Classification types 2, 4, and 5 are high density polyethylene, low density polyethylene and polypropylene, respectively. Any combination of the polyethylene and polypropylene waste plastics can be used. For the present process, at least some polypropylene waste plastic is preferred. Polystyrene, classification 6, can also be present in a limited amount.

Proper sorting of waste plastics is very important in order to minimize contaminants such as N, Cl, and S. Plastics waste containing polyethylene terephthalate (plastics recycle classification type 1), polyvinyl chloride (plastics recycle classification type 3) and other polymers (plastics recycle classification type 7) need to be sorted out to less than 5%, preferably less than 1% and most preferably less than 0.1%. The present process can tolerate a moderate amount of polystyrene (plastics recycle classification type 6). Waste polystyrene needs to be sorted out to less than 20%, preferably less than 10% and most preferably less than 5%.

Washing of waste plastics can remove metal contaminants such as sodium, calcium, magnesium, aluminum, and non-metal contaminants coming from other waste sources. Non-metal contaminants include contaminants coming from the Periodic Table Group IV, such as silica, contaminants from Group V, such as phosphorus and nitrogen compounds, contaminants from Group VI, such as sulfur compounds, and halide contaminants from Group VII, such as fluoride, chloride, and iodide. The residual metals, non-metal contaminants, and halides need to be removed to less than 50 ppm, preferentially less than 30 ppm and most preferentially to less than 5 ppm.

If the washing does not remove the metals, non-metal contaminants, and halide impurities adequately, then a separate guard bed can be used to remove the metals and non-metal contaminants.

The petroleum with which the waste plastic is blended is generally a petroleum feedstock for the refinery. It is preferred that the petroleum blending oil is the same as the petroleum feedstock for the refinery. The petroleum can also comprise any petroleum derived oil or petroleum based material. In one embodiment, the petroleum feedstock oil can comprise atmospheric gas oil, vacuum gas oil (VGO), atmospheric residue, or heavy stocks recovered from other refinery operations. In one embodiment, the petroleum feedstock oil with which the waste plastic is blended comprises VGO. In one embodiment the petroleum feedstock oil with which the waste plastic is blended comprises light cycle oil (LCO), heavy cycle oil (HCO), FCC naphtha, gasoline, diesel, toluene, and/or an aromatic solvent derived from petroleum.

Figure 5:
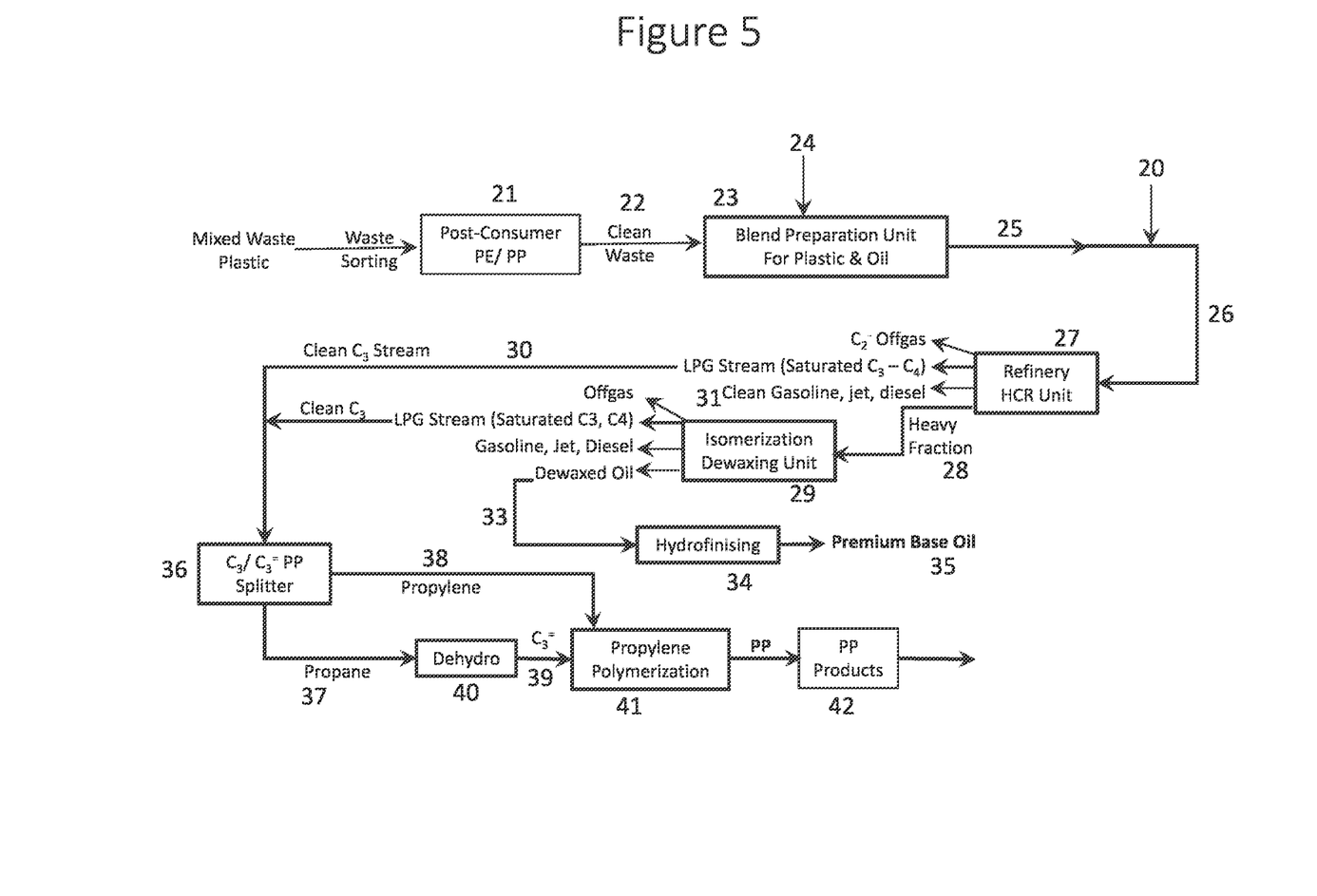
FIG. 5 depicts a present process where the prepared blend is passed to a refinery hydrocracking unit.

FIG. 5 shows one embodiment of a present integrated process, where the blend is sent to a hydrocracking unit. The same numbers in FIG. 5 that correspond to FIGS. 2 and 3 refer to the same items/units. As shown, selected waste 21 is cleaned 22 and then passed to a blend preparation unit 23, where the plastic and refinery feedstock 24, are blended to create a hot blend of the plastic and oil 25. To this blend, when desired, an oil refinery feedstock such as Vacuum Gas Oil (VGO) 20 is added. If the blend of plastic/oil is still hot, (25 in FIG. 2) then it can be mixed with the co-feed oil 20 immediately. However, if the stable blend of plastic/oil needs heating due to storage or transportation (102 in FIG. 3) the blend is generally heated, for example, with a preheater (preheater 50 in FIG. 3) to a temperature above the melting point of the plastic before mixing with the co-feed crude oil. This homogeneous plastic/oil blend and crude oil 26 is then sent to a hydrocracking unit 27 in a refinery. In another embodiment, the heated blend and the VGO co-feed are each passed directly, but separately, to the hydrocracking unit.

The refinery will generally have its own hydrocarbon feed flowing through the refinery units. In this case, as shown in FIG. 5, the hydrocarbon feed is VGO 20. The flow volume of blend to the refinery units, here a hydrocracking unit, can comprise any practical or accommodating volume % of the total flow to the refinery units. Generally, the flow of the blend, for practical reasons, can be up to about 50 vol. % of the total flow, i.e., the refinery flow and the blend flow. In one embodiment, the flow of the blend is an amount up to about 100 vol. % of the total flow. In another embodiment, the volume flow of the blend is an amount up to about 25 vol. % of the total flow. About 50 vol. % has been found to be an amount that is quite practical in its impact on the refinery while also providing excellent results and being an amount that can be accommodated. Avoiding any negative impact on the refinery and its products is important. If the amount of the plastic in the final blend is greater than 20 wt. % of the final blend, difficulties in refinery unit operations might ensue. By the final blend is meant the present plastic/oil blend and any co-feed petroleum. The plastic/oil blend can comprise up to 100 vol. % of the feed to the refinery units, in which case it is the final blend.

Any suitable hydrocracking operation can be run. The catalyst in the hydrocracker can be selected from any known hydrocracking catalysts. The hydrocracking conditions generally include a temperature in the range of from 175° C. to 485° C., molar ratios of hydrogen to hydrocarbon charge from 1 to 100, a pressure in the range of from 0.5 to 350 bar, and a liquid hourly space velocity (LHSV) in the range of from 0.1 to 30. Larger molecules are cracked into smaller molecules in the hydrocracking reactor. Hydrocracking catalysts normally contain a large pore zeolite such as USY, and various combinations of Group VI and VIII base metals such as nickel, cobalt, molybdenium and tungsten, which are finely dispersed on an alumina or oxide support.

From the hydrocracking unit 27 is recovered a LPG $C_3$-$C_4$ stream 30, a clean naphtha stream 31 comprising gasoline, jet and diesel fuel fractions, and a heavy fraction 28. The heavy fraction 28 is passed to an isomerization/dewaxing unit 29. Within the hydrocracking reactor, the feed may first be contacted with a hydrotreating catalyst under hydrotreating conditions in a hydrotreating zone or guard layer to provide a hydrotreated feedstock. Contacting the feedstock with the hydrotreating catalyst in a guard layer may serve to effectively hydrogenate aromatics in the feedstock, and to remove N- and S-containing compounds from the feed, thereby protecting the hydroisomerization catalysts of the catalyst system. A hydrogenation catalyst normally contains various combinations of Group VI and VIII base metals such as nickel, cobalt, molybdenium and tungsten, which are finely dispersed on an alumina or oxide support. By "effectively hydrogenate aromatics" is meant that the hydrotreating catalyst is able to decrease the aromatic content of the feedstock by at least about 20%. The hydrotreated feedstock may generally comprise $C_{10+}$ n-paraffins and slightly branched isoparaffins, with a wax content of typically at least about 20%.

Hydroisomerization catalysts useful in the present processes typically will contain a catalytically active hydrogenation metal. The presence of a catalytically active hydrogenation metal leads to product improvement, especially VI and stability. Typical catalytically active hydrogenation metals include chromium, molybdenum, nickel, vanadium, cobalt, tungsten, zinc, platinum, and palladium. The metals platinum and palladium are especially preferred, with platinum most especially preferred. If platinum and/or palladium is used, the total amount of active hydrogenation metal is typically in the range of 0.1 wt. % to 5 wt. % of the total catalyst, usually from 0.1 wt. % to 2 wt. %. In addition, a hydroisomerization catalyst normally contains a medium pore size zeolite such as ZSM-23, ZSM-48, ZSM-35, SSZ-32, SSZ-91 dispersed on an oxide support.

The refractory oxide support may be selected from those oxide supports, which are conventionally used for catalysts, including silica, alumina, silica-alumina, magnesia, titania and combinations thereof.

The conditions in the isomerization/dewaxing reactor unit 29 will generally include a temperature within a range from about 390° F. to about 800° F. (199° C. to 427° C.). In an embodiment, the hydroisomerization dewaxing conditions includes a temperature in the range from about 550° F. to about 700° F. (288° C. to 371° C.). In a further embodiment, the temperature may be in the range from about 590° F. to about 675° F. (310° C. to 357° C.). The total pressure may be in the range from about 500 to about 3000 psig (0.10 to 20.68 MPa), and typically in the range from about 750 to about 2500 psig (0.69 to 17.24 MPa).

From the isomerization/dewaxing unit 29 a dewaxed oil 33 can be recovered, which oil can be used as a base oil. The oil can also be passed to a hydrofinishing unit 34 to prepare a premium base oil 35. In the hydrofinishing unit 34, the hydrofinishing may be performed in the presence of a hydrogenation catalyst, as is known in the art. The hydrogenation catalyst used for hydrofinishing may comprise, for example, platinum, palladium, or a combination thereof on an alumina support. The hydrofinishing may be performed at a temperature in the range from about 350° F. to about 650° F. (176° C. to 343° C.), and a pressure in the range from about 400 psig to about 4000 psig (2.76 to 27.58 1 MPa). Hydrofinishing for the production of lubricating oils is described, for example, in U.S. Pat. No. 3,852,207, the disclosure of which is incorporated by reference herein.

The LPG stream 30 can be passed to a PP splitter 36. The naphtha stream 31 can be passed in whole or in part to gasoline pools or upgrading processes in order to upgrade the fuel fractions. Jet fuel can be recovered from the upgrading processes. A portion of the naphtha can also be passed to the PP splitter, if desired.

The PP splitter 36 produces streams of propane 37 and propylene 38. The propylene 38 is fed to a propylene polymerization unit 41 to produce polypropylene. The pure propane 37 can be fed to a propane dehydrogenation unit 40 to make additional propylene 39, and then ultimately polypropylene in the propylene polymerization unit 41. The polypropylene polymer made in the propylene polymerization unit 41, can be made into consumer products 42.

Dehydrogenation of propane is practiced widely in the industry to produce propylene. The reaction is endothermic, conversion is maintained by multi-stage reactors and interstage heaters. The unit typically operates at high temperature (>900° F.) and low pressure (<50 psig) in the presence of noble metal (Pt) catalyst. The multi-stage process generates approximately 85% purity propylene/propane mixture. This stream is directed to a propane/propylene (PP) splitter which is a high efficiency distillation column. The splitter produces pure propylene stream with 99.5-99.8% purity.

The PP splitter unit and/or propane dehydrogenation unit can be located away from a refinery, near a refinery, or within a refinery. The propane/propylene mix is sent to the PP splitter by truck, barge, rail car or pipeline. It is preferred that the PP splitter unit and propane dehydrogenation unit are in close proximity to the refinery hydrocracking unit.

Polypropylene is produced via chain-growth polymerization from the monomer propylene. A Ziegler-Natta catalyst or metallocene catalyst is used to catalyze the polymerization of propylene to polypropylene polymer with desired properties. These catalysts are activated with special cocatalyst containing an organoaluminum compounds. The industrial polymerization processes uses either gas phase polymerization in a fluidized bed reactor or bulk polymerization in loop reactors. The gas phase polymerization typically runs at 50-90° C. temperature and a pressure of 8-35 atm pressure in the presence of $H_2$. The bulk polymerization proceeds at 60 to 80° C. and 30-40 atm pressure is applied to keep the propylene in liquid state.

The propylene polymerization unit 41 is preferably located near the refinery so that the feedstock (propylene) can be transferred via pipeline. For a petrochemical plant located away from the refinery, the feedstock can be delivered via truck, barge, rail car or pipeline.

The benefits of a circular economy and an effective and efficient recycling campaign are realized by the present integrated process.

The following examples are provided to further illustrate the present process and its benefits. The examples are meant to be illustrative and not limiting.

Example 1

Properties of Plastic Samples, and Feedstocks Used for Blend Preparations

Four plastic samples, low density polyethylene (LDPE, Plastic A), high density polyethylene (HDPE, Plastic B), two polypropylene samples with average molecular weight of 12,000 (PP, Plastic C) and ~250,000 (PP, Plastic D) were purchased, and their properties are summarized in Table 1.

TABLE 1

Properties of Plastics Used

| | LDPE (Plastic A) | HDPE (Plastic B) | PP (Plastic C) | PP (Plastic D) |
|---|---|---|---|---|
| Form | Pellets | Pellets | Pellets | Pellets |
| Melt Index | 25 g/10 min (190° C./ 2.16 kg) | 12 g/10 min (190° C./ 2.16 kg) | — | 12 g/10 min (230° C./ 2.16 kg) |
| Melting Point, ° C. | 116 | 125-140 | 157 | 160-165 |
| Transition Temp, ° C. | 93, softening | 125, softening | 163, softening | — |
| Density, g/mL at 25° C. | 0.925 | 0.952 | 0.9 | 0.9 |
| Hardness | — | 66 | — | 100 |
| Average molecular weight, $M_w$ | — | — | ~12,000 | ~250,000 |
| Average molecular weight, $M_n$ | — | — | ~5,000 | ~67,000 |

Petroleum feedstocks used to prepare the stable blends with plastic include hydrotreated vacuum gas oil (VGO), Aromatic 100 solvent, light cycle oil (LCO), and diesel. Their properties are shown in Table 2 below. Aromatic 100 is a commercially available aromatic solvent manufactured from petroleum-based material, and mainly contains C9-C10 dialkyl and trialkyl benzenes.

TABLE 2

Properties of Petroleum Feedstocks for Blend Preparation

| | Hydrotreated VGO Petroleum Feed #1 | Aromatic 100 Petroleum Feed #2 | LCO Petroleum Feed #3 | Diesel Petroleum Feed #4 |
|---|---|---|---|---|
| Specific Gravity | 0.897 | 0.872 | 0.956 | 0.811 |
| Carbon, wt % | 87.84 | 89.90 | 90.50 | 86.4 |
| Hydrogen, wt % | 12.69 | 10.10 | 9.50 | 14.6 |
| H/C Molar Ratio | 1.73 | 1.33 | 1.26 | 2.0 |
| Bromine Number | 2 | — | — | 0.1 |
| Total S, ppm | 150 | 0 | 900 | <2 |
| Total N, ppm | 273 | 0 | N/A | <0.1 |
| Ni, ppm | <0.6 | 0 | <0.2 | <0.2 |
| V, ppm | <0.6 | 0 | <0.2 | <0.2 |
| Simdist, ° F. IBP (0.5%) | 462 | 297 | 235 | 536 |
| 5 wt % | 573 | 325 | 405 | 553 |
| 10 wt % | 616 | 327 | 441 | 563 |
| 30 wt % | 706 | 330 | 490 | 601 |
| 50 wt % | 775 | 336 | 541 | 638 |
| 70 wt % | 854 | 344 | 607 | 673 |
| 90 wt % | 962 | 355 | 689 | 702 |
| 95 wt % | 1008 | 362 | 718 | 709 |
| FBP (99.5%) | 1107 | 376 | 786 | 717 |

Figure 6:
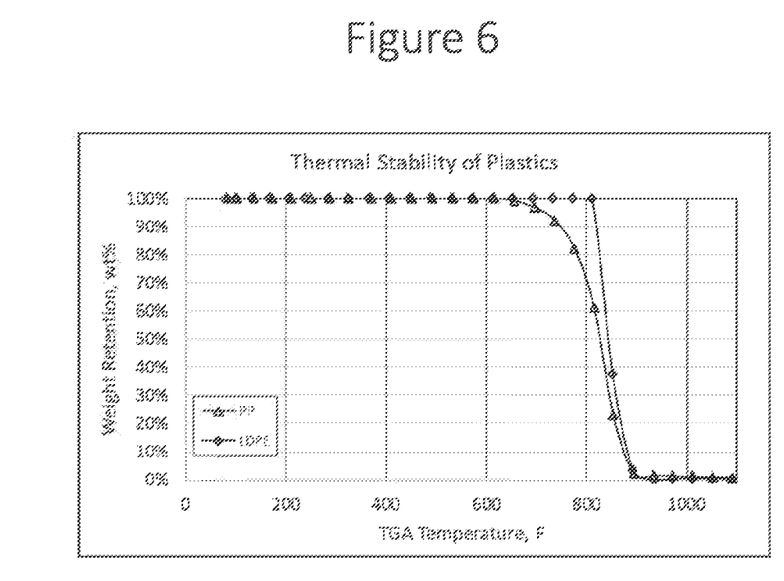
FIG. 6 graphically depicts a thermal gravimetric analysis (TGA) of the thermal stability of polyethylene and polypropylene.

Thermal Gravimetric Analysis (TGA) was conducted with Plastic A (LDPE) and Plastic C (Polypropylene) to verify the plastic materials are thermally stable well above the melt preparation temperature. TGA results shown in FIG. 6 indicate the LDPE sample is stable up to 800° F. and the polypropylene sample up to 700° F.

Example 2

Feedstocks of $C_3$-$C_4$ and/or Naphtha Generation from Waste Plastics/Oil Blend Cofeeding to Refinery Hydrocracking Unit By feeding the present plastic/oil blend, with or without a cofeed, to a hydrocracking unit, the blend will be converted and fractionated into multiple components. The refinery hydrocracking unit produces substantial amounts of clean propane, butane, and naphtha streams, as well as other streams for refinery conversion units and polypropylene production.

Example 3

Hydroracking of Plastic and Petroleum Oil Blend for Production of Fuels and Base Oil with Recycle Contents and Low $CO_2$ Footprint Gasoline, jet fuel, diesel, and heavy cuts from the hydrocracker effluent distillation column can each be sent to the corresponding blending pool to be blended to a finished gasoline, jet fuel, diesel or marine oil with recycle contents and a lower $CO_2$ footprint. Portions of the heavy fraction can be further processed in an isomerization/dewaxing unit to prepare base oil or white oil with a recycle content and a lower $CO_2$ footprint (FIG. 5).

Example 4

Feeding of Recycle $C_3$-$C_4$ to PP Splitter for Propylene Production, Followed by Production of Polypropylene Resin and Polypropylene Consumer Products and Base Oil The propane and butane stream, produced via cofeeding of a plastic/oil blend to a hydrocracking unit per Example 2, are good feedstocks to cofeed to a PP splitter for production of propylene with a recycle content. At least a portion of the streams, if not all, can be fed to the PP splitter. The propylene can be processed in a polymerization unit to produce polypropylene resin containing some recycled-polyethylene/polypropylene derived materials while the quality of the newly produced polypropylene will be indistinguishable to the virgin polypropylene made entirely from virgin petroleum resources. The polypropylene resin with the recycled material can then be further processed to produce various polypropylene products to fit the needs of consumer products. These polypropylene consumer products would now contain chemically recycled, circular polymer while the quality of the polypropylene consumer products would be indistinguishable from those made entirely from virgin polypropylene polymer. These chemically recycled polymer products are different from mechanically recycled polymer products whose qualities are inferior to the polymer products made from virgin polymers.

A heavy fraction from the hydrocracking unit can also be passed to an isomerization/dewaxing unit. Dewaxed oil, or base oil, can be recovered from the unit, which base oil can be further passed to a hydrofinishing unit to prepare premium base oil or white oil.

As used in this disclosure the word "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the composition. The phrase "consisting of" or "consists of" is intended as a transition meaning the exclusion of all but the recited elements with the exception of only minor traces of impurities.

All patents and publications referenced herein are hereby incorporated by reference to the extent not inconsistent herewith. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise that as specifically described without actually departing from the spirit and scope of the present invention as defined by the appended claims.

What is claimed is:

1. A process for converting waste plastic into chemicals useful in preparing polypropylene, comprising:
   (a) selecting waste plastics containing polyethylene and/or polypropylene;
   (b) preparing a liquid blend of petroleum and the selected plastic, with the blend comprising less than 20 wt. % of the selected plastic; and
   (c) passing the blend to a hydrocracking unit in a refinery.

2. A continuous process for converting waste plastic into recycle for preparation of base oil comprising:
   (a) selecting waste plastics comprising polyethylene and/or polypropylene;
   (b) preparing a liquid blend of petroleum and the selected waste plastic with the blend comprising less than 20 wt. % of the selected waste plastic;
   (c) passing the blend at a temperature above the melting point of the plastic to a feed pretreater unit for a refinery hydrocracking unit;
   (d) recovering a heavy fraction from the hydrocracking unit and passing the heavy fraction to an isomerization dewaxing unit; and
   (e) recovering base oil from the isomerization/dewaxing unit.

3. The process of claim 2, wherein the base oil recovered from the isomerization dewaxing unit is passed to a hydrofinishing unit.

4. A continuous process for converting waste plastic into recycle for preparation of lower carbon footprint fuels and base oil comprising:
   (a) selecting waste plastics comprising polyethylene and/or polypropylene;
   (b) preparing a liquid blend of petroleum and the selected waste plastic with the blend comprising less than 20 wt. % of the selected waste plastic;
   (c) passing the blend at a temperature above the melting point of the plastic in the blend to a refinery hydrocracking unit;
   (d) recovering a heavy fraction from the hydrocracking unit and passing the heavy fraction to a refinery isomerization/dewaxing unit; and
   (e) recovering base oil from the isomerization dewaxing unit.

5. The process of claim 4, wherein the lower carbon footprint fuels includes gasoline, jet fuel, diesel, and/or marine oil.

6. A continuous process for converting waste plastic into recycle for polypropylene polymerization comprising:
   (a) selecting waste plastics comprising polyethylene and/or polypropylene;
   (b) preparing a liquid blend of petroleum and the selected waste plastic with the blend comprising less than 20 wt. % of the selected waste plastic;
   (c) passing the blend at a temperature above the melting point of the plastic to a hydrocracking unit in a refinery;
   (d) recovering a liquid petroleum gas $C_3$ olefin/paraffin mixture from the refinery hydrocracking unit;
   (e) separating the $C_3$ paraffin and $C_3$ olefin into different fractions; and
   (f) passing the $C_3$ olefin to a propylene polymerization reactor.

7. The process of claim 6, wherein a naphtha fraction is recovered from the refinery hydrocracking unit.

8. The process of claim 7, wherein a portion of the naphtha stream recovered from the hydrocracking unit is further processed in the refinery to clean gasoline, diesel, and/or jet fuel.

9. The process of claim 8, wherein jet fuel is recovered from the further processing in the refinery.

10. The process of claim 6, wherein the blend of (b) is a hot homogeneous blend of waste plastic and petroleum oil.

11. The process of claim 6, wherein the liquid blend of (b) is prepared from a stable blend of waste plastic and petroleum oil.

12. The process of claim 11, wherein the stable blend of petroleum and selected waste plastic is prepared by heating the waste plastic above the melting point of the plastic and mixing with the petroleum, and then cooling the blend to a temperature below the melting point of the waste plastic.

13. The process of claim 6, wherein polypropylene products are prepared from the polymerized propylene.

14. The process of claim 6, wherein the waste plastics selected in (a) comprise plastics from classification group 2, 4, and/or 5.

15. The process of claim 14, wherein the waste plastics selected in (a) comprise less than 5 wt. % plastics from classification groups 1, 3, and 7.

16. The process of claim 14, wherein the waste plastics selected in (a) comprise less than 0.1 wt. % of plastics form classification groups 1, 3, and 7.

17. The process of claim 14, wherein less than 50 ppm of halides is in the selected plastics.

18. The process of claim 6, wherein a gasoline fraction is recovered from the refinery hydrocracking unit and is sent to a gasoline blending pool.

19. The process of claim 6, wherein the volume flow of the blend to the refinery hydrocracking unit in (c) comprises up to 100 volume % of the total hydrocarbon flow to the hydrocracking unit.

20. The process of claim 6, wherein the volume flow of the blend to the refinery hydrocracking unit in (c) comprises up to 50 volume % of the total hydrocarbon flow to the hydrocracking unit.

21. The process of claim 20, wherein the blend flow comprises up to 25 volume % of the total flow to the hydrocracking unit.

22. The process of claim 21, wherein the blend in (b) comprises about 10 wt. % or less of the selected waste plastic.

23. The process of claim 20, wherein the blend in (b) comprises about 10 wt. % or less of the selected waste plastic.

24. The process of claim 6, wherein the petroleum in the blend comprises atmospheric gas oil, vacuum gas oil (VGO), atmospheric residue, a petroleum derived oil, a petroleum based material, and/or heavy stock recovered from refinery operations.

25. The process of claim 6, wherein the petroleum in the blend comprises light cycle oil (LCO), heavy cycle oil (HCO), FCC naphtha, gasoline, diesel, toluene, and/or aromatic solvent derived from petroleum.

26. The process of claim 6, wherein a heavy fraction is recovered from the hydrocracking unit and passed to an isomerization/dewaxing unit.

27. The process of claim 26, wherein a base oil is recovered from the isomerization/dewaxing unit.

28. The process of claim 27, where the recovered base oil is passed to a hydrofinishing unit.

29. The process of claim 26, wherein a naphtha fraction is recovered from the isomerization/dewaxing unit, and at least a portion of the naphtha fraction is passed to a PP splitter to recover propylene.

30. The process of claim 6, wherein the blend in (b) comprises about 10 wt. % or less of the selected waste plastic.

31. The process of claim 6, wherein the amount of the plastic passed to the refinery hydrocracking unit comprises less than 10 wt % of the blend and any co-feed petroleum to the refinery hydrocracking unit.

* * * * *